(12) United States Patent
Munn

(10) Patent No.: US 7,913,687 B2
(45) Date of Patent: *Mar. 29, 2011

(54) ORAL AIRWAY

(76) Inventor: Myron L. Munn, Beatrice, NE (US)

(*) Notice: Subject to any disclaimer, the term of this patent is extended or adjusted under 35 U.S.C. 154(b) by 927 days.

This patent is subject to a terminal disclaimer.

(21) Appl. No.: 11/584,978

(22) Filed: Oct. 23, 2006

(65) Prior Publication Data

US 2008/0185004 A1    Aug. 7, 2008

(51) Int. Cl.
*A61M 16/00* (2006.01)
*A62B 9/06* (2006.01)

(52) U.S. Cl. ............................. 128/200.26; 128/207.14

(58) Field of Classification Search ............. 128/207.14, 128/200.24, 200.26, 204.18, 207.15–207.17
See application file for complete search history.

(56) References Cited

U.S. PATENT DOCUMENTS

| | | | |
|---|---|---|---|
| 2,127,215 A | 8/1938 | Gwathmey | |
| 2,599,521 A | 6/1952 | Berman | |
| 2,705,959 A | 4/1955 | Elmore | |
| 3,306,298 A | 2/1967 | Raimo | |
| 3,398,747 A | 8/1968 | Raimo | |
| 3,419,004 A * | 12/1968 | Berman | 128/207.14 |
| 3,568,680 A | 3/1971 | Raimo | |
| 3,576,187 A | 4/1971 | Oddera | |
| 3,756,244 A | 9/1973 | Kinnear et al. | |
| 3,908,665 A | 9/1975 | Moses | |
| 3,926,196 A | 12/1975 | Bornhorst et al. | |
| 3,930,507 A | 1/1976 | Berman | |
| D261,442 S | 10/1981 | Anderson | |
| 4,363,320 A | 12/1982 | Kossove | |
| 4,553,540 A * | 11/1985 | Straith | 128/200.26 |
| 4,919,126 A | 4/1990 | Baildon | |
| 6,196,224 B1 | 3/2001 | Alfery | |
| 6,679,901 B1 * | 1/2004 | Takuma | 606/196 |
| 6,901,928 B2 * | 6/2005 | Loubser | 128/200.26 |
| 2005/0016531 A1 * | 1/2005 | Takuma | 128/200.26 |
| 2007/0267024 A1 * | 11/2007 | Kremer et al. | 128/207.14 |
| 2008/0092900 A1 * | 4/2008 | Munn | 128/207.14 |

* cited by examiner

*Primary Examiner* — Justine R Yu
*Assistant Examiner* — Rachel T Young
(74) *Attorney, Agent, or Firm* — Dennis L. Thomte; Thomte Patent Law Office LLC

(57) ABSTRACT

An oral airway for providing an air passage to a patient's trachea. The oral airway includes a curved section and a straight section with the curved section having spaced-apart curved upper and lower members and the straight section having spaced-apart planar upper and lower members with the same width. The curved upper member has the same width as the planar upper member with the curved lower member having a greater width than the width of the lower planar member. The width of the curved lower member is greater than the width of the planar lower member and the distance between the curved upper and lower members is greater than the distance between the planar upper and lower members. The curved lower member has a generally inverted V-shaped cross-section.

2 Claims, 3 Drawing Sheets

ORAL AIRWAY

BACKGROUND OF THE INVENTION

1. Field of the Invention

This invention relates to an oral airway and more particularly to an oral airway which truly represents an improvement in the oral airway art.

2. Description of the Related Art

In modern anesthesia practice, oral airways are used primarily for two reasons. The first reason is that after intubation of the trachea, an oral airway is placed to prevent a patient from biting down on the endotracheal tube and thus occluding the endotracheal tube. The second and primary reason for the use of an oral airway in the practice of aesthesia is to elevate the tongue against the floor of the mouth to create a larger opening in the mouth to facilitate the utilization of positive pressure ventilation using an anesthesia mask after a patient has been given medications to induce general anesthesia. The drugs normally used to induce general anesthesia may greatly decrease or altogether stop the patient's own spontaneous respiratory effort. Therefore, the Anesthesia Practitioner must immediately begin assisting or controlling the patient's ventilation.

It has been noted that patients undergoing general anesthesia have occasional difficulties in maintaining the a patient's airway and the ability to ventilate the patient. It has been observed that patients of all ages which were difficult to ventilate with an anesthesia mask after induction of general anesthesia. This has happened even after proper placement of the recommended size of oral airway. Anyone who has practiced anesthesia for some time has experienced the same difficulties. Anesthesia Practitioners are all taught the "tricks of the trade" in how to ventilate patients after induction of general anesthesia including a variety of physical adjustments to the anesthetized patient such as elevation of the jaw and extension of the patient's neck. If the patient cannot be adequately ventilated after induction of general anesthesia, life-threatening problems may develop such as hypoxia, hypercarbia, cardiac arrhythmias and even death.

Once general anesthesia has been induced, one of the main impediments to adequately ventilating a patient with positive pressure ventilation, after placement of an oral airway, is the relaxation of the soft tissue structures in the hypo-pharynx. These structures tend to collapse, thus obstructing airflow. This inward collapsing occurs both front to back and side to side, thus greatly decreasing the size of the oral opening through which the Anesthesia Practitioner may ventilate the patient. This anatomical relaxation is fairly consistent with every patient who undergoes a general anesthetic. However, there is a physical characteristic of some patients which greatly increases the difficulty of mask ventilation—that characteristic is obesity. Applicant has noted the increasing incidence of obesity in both the pediatric and adult population. These obese patients present an increased level of difficulty to the Anesthesia Practitioner in the area of airway management. Obese patients tend to have larger, thicker tongues along with more redundant soft tissue in the oropharyngeal area. Obese patients also tend to have thicker necks, so it is more difficult to hyperextend the neck and lift the jaw to facilitate adequate ventilation after general anesthesia is induced. In discussions with other Anesthesia Practitioners, the inventor has perceived a common concern that the oral airways currently available do not adequately address the growing problem of obesity in the population.

As stated, it is well known to utilize an oral airway for the purpose of aiding the breathing of unconscious patients. Reference may be made to U.S. Pat. No. 2,599,521, which issued Jun. $3^{rd}$, 1952, to R. A. Berman, for a description of a conventional oral airway now known in medical practice as the Berman Oral Airway. The Berman Oral Airway, and later devices modeled after it, is employed in the practice of anesthesia and other areas of respiratory medicine by insertion of the oral airway into the mouth and pharynx of a patient to provide a channel for respiratory purposes, particularly in unconscious patients such as those who have been administered a general anesthetic. It is the purpose of the oral airway to prevent respiratory obstruction by preventing collapse of the pharyngeal tissues and/or obstruction of the pharynx by the tongue.

The Berman Oral Airway and later devices are available to the medical professional in a number of different sizes for use in all sizes of patients from premature infants to large adults. However, each size constitutes a unitary member which may not itself be adjusted in size, shape, or contour. Thus, conventional airways are substantially rigid structures which may not be altered in use to fit particular patients, particular problems, or unusual anatomic anomalies or structures. The Berman Oral Airway has served Anesthesia Practitioners well for many years, but the physical characteristics of patients have changed since 1952 while the Berman Oral Airway remains the same.

The Berman Oral Airway comes in various sizes from 40 mm to 100 mm in incremental steps of 10 mm (i.e., 40 mm, 50 mm, 60 mm, 70 mm, 80 mm, 90 mm, and 100 mm). These sizes are roughly correlated to general anatomic dimension described as the distance from the exterior of the front teeth to the back of the oropharynx. So, correspondingly, a 40 mm Berman Oral Airway is probably an appropriate size for a premature infant whereas a 100 mm Berman Oral Airway is probably appropriate for a large adult, and a 90 mm Berman Oral Airway is generally used on a medium adult patient. If the patient is very obese and has a thick tongue and has a large amount of soft tissue in the oropharynx, the 90 mm oral airway may not adequately elevate the tongue because it is not wide enough side to side to provide enough support for the tongue. In this case, a 100 mm Berman Oral Airway (which is wider side to side) may provide the additional support for the tongue that is needed to open the airway, but it cannot be used because the longer structure of the airway (100 mm) may not fit in the patient's mouth. The 100 mm oral airway would extend too far outside of the patient's mouth, thus placing an anesthesia mask over the patient's face to obtain a good mask seal in order to ventilate the patient with positive pressure would be very difficult, if not impossible. The usual scenario is someone who is of very short stature and very obese. These people many times need the width and depth of a 100 mm Berman Oral Airway, but the length of an 80 mm Berman Oral Airway. This would greatly facilitate the ability to ventilate this patient after induction of general anesthesia. This problem has been overcome in the past by actually inserting two 80 mm Berman Oral Airways on these types of patients or sometimes one 90 mm Berman Oral Airway and one 80 mm Berman Oral Airway. In this way you are able to achieve enough side to side tongue support to adequately ventilate the patient until you are ready to place an LMA or intubate the patient. Inserting two airways into the patient is sometimes adequate but can be awkward. Therefore, a new type of airway is needed for these patients.

SUMMARY OF THE INVENTION—THE BUTTERFLY ORAL AIRWAY

Accordingly, the present invention provides modifications to the Berman Oral Airway which will provide better elevation of the tongue against the floor of the mouth by way of: 1) a longer middle support distance which increases the distance the tongue is elevated against the floor of the mouth thus increasing the anterior-posterior dimension of the airway opening; 2) the greater width of the curved lower member of the curved section of the oral airway which will give better support to the tongue laterally, thus increasing the side to side dimension of the airway opening; and 3) the elevation of the lower curved member of the curved section of the airway into an inverted "V" shape which will also greatly increase the lateral support of the tongue.

By altering these three characteristics of the Berman Oral Airway, but not altering the length or the radius of the curve of the airway, the instant airway sizes would be interchangeable with the Berman Oral Airway sizes. For instance, in a situation where you would normally use an 80 mm Berman Oral Airway, the 80 mm airway of this invention would be appropriate, but would give better tongue support and consequently a larger opening of the patient's airway to facilitate easier ventilation of the patient. This would be especially helpful in obese patients with large tongues, but would also be useful for all patients being administered general anesthesia.

More particularly, the oral airway of this invention comprises a straight section having inner and outer ends adapted to fit between the patient's teeth and a curved section adapted to fit over the patient's tongue and extending to the oropharyngeal area. The straight section of the oral airway includes a substantially planar upper member and a substantially planar lower member which are spaced-apart by a medial web extending therebetween. The planar upper and lower members of the straight section have substantially the same widths. The outer end of the planar upper member has a flange extending upwardly therefrom and the outer end of the planar lower member has a flange extending downwardly therefrom. The flanges externally overlie the lips of the patient. The curved section of the airway comprises spaced-apart curved upper and lower members which are spaced-apart by a medial web extending therebetween. The curved upper member of the curved section has substantially the same width as the planar upper member of the straight section. The curved lower member of the curved section has a generally inverted V-shaped cross-section and has a greater width for substantially its entire length than the planar lower member of the straight section. In the preferred embodiment of the oral airway described above, the distance between the curved upper and lower members of the curved section, at either side of the medial web, is greater than the distance between the planar upper and lower members of the straight section for substantially the entire length thereof. The oral airway of this invention may be either a 100 mm, 90 mm, 80 mm, 70 mm, 60 mm, 50 mm, or 40 mm size.

It is therefore a principal object of the invention to provide an improved oral airway to provide an air passage to the patient's trachea.

A further object of the invention is to provide an improved oral airway which will provide better elevation of the tongue against the floor of the mouth by way of: 1) a longer middle support distance which increases the distance the tongue is elevated against the floor of the mouth, thus increasing the anterior-posterior dimension of the airway opening; 2) the greater width of the curved lower member of the curved section of the oral airway which will give better support to the tongue laterally, thereby increasing the side to side dimension of the airway opening; and 3) the elevation of the lower curved member of the curved section of the airway into an inverted "V" shape which will also greatly increase the lateral support of the tongue.

These and other objects will be apparent to those skilled in the art.

DETAILED DESCRIPTION OF THE INVENTION

Figure 2:
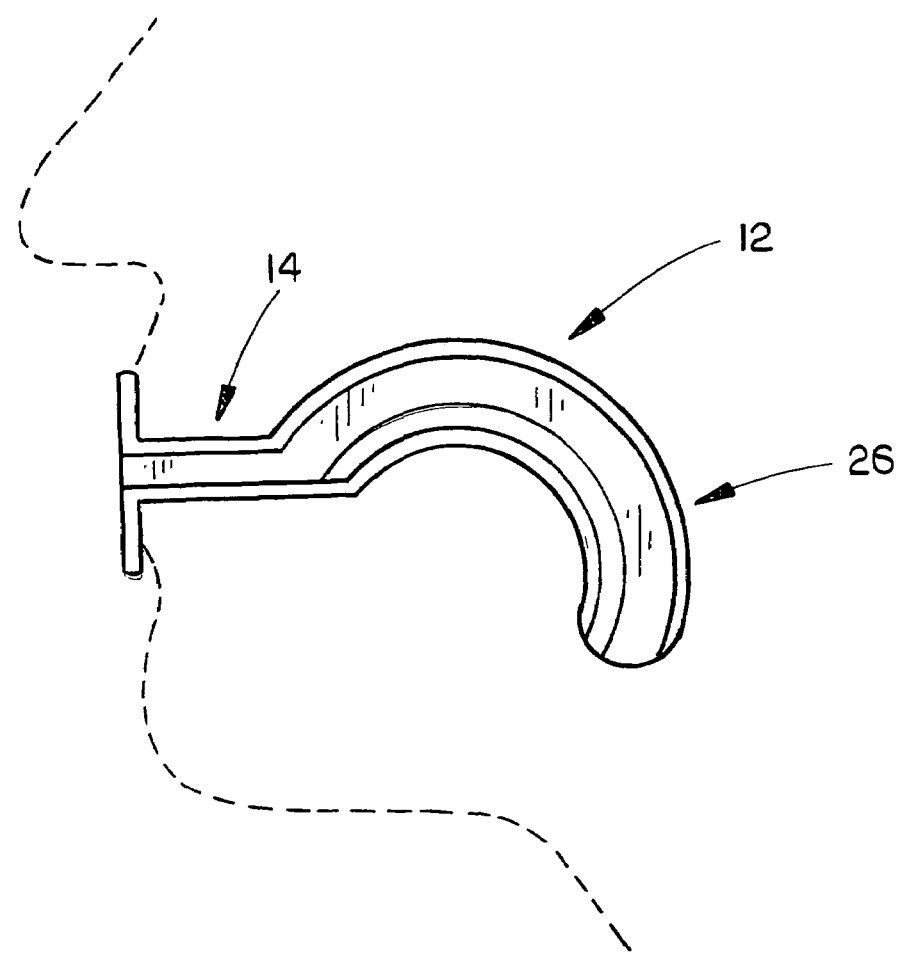
FIG. 2 is a side sectional view of the oral airway of this invention inserted into the patient's mouth.
Figure 1:
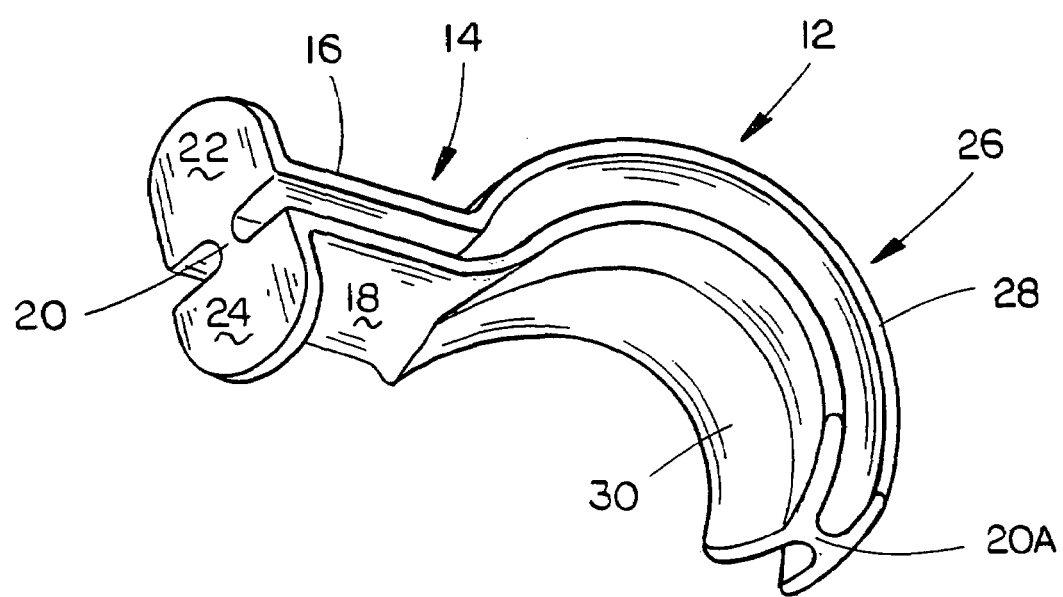
FIG. 1 is a bottom perspective view of the oral airway of this invention.
Figure 4:
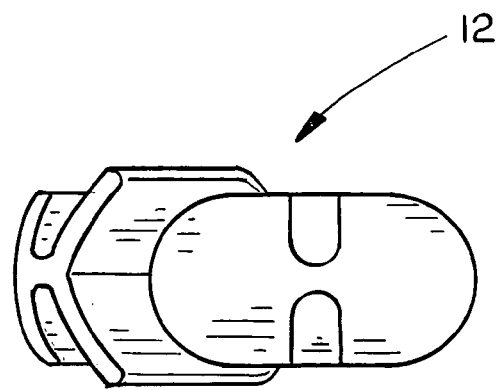
FIG. 4 is a top view of the oral airway of FIG. 1.
Figure 3:
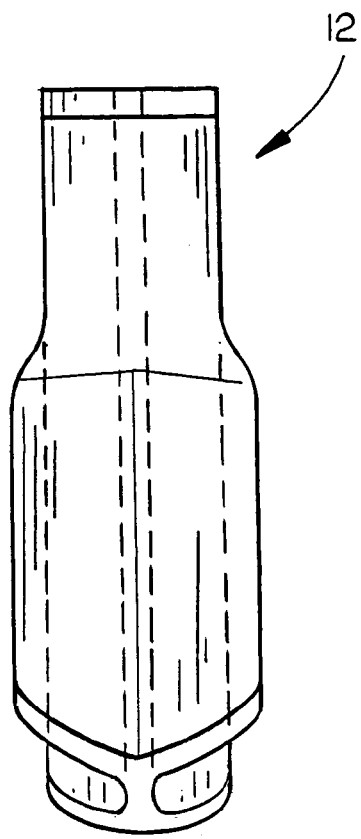
FIG. 3 is a bottom elevational view of the airway of FIG. 1.
Figure 5:
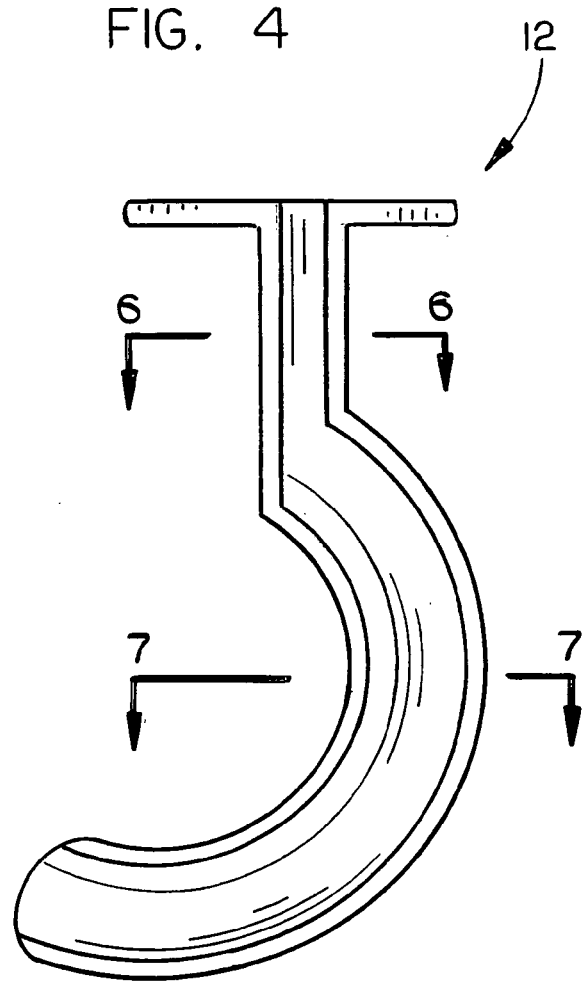
FIG. 5 is a side view of the oral airway of FIG. 1.

In the drawings, the numeral 12 refers generally to the preferred embodiment of this invention. Airway 12 includes a straight section 14 having an upper planar member 16 and a lower planar member 18 which are spaced-apart by means of a medial web or rib 20. Flange 22 extends upwardly from the outer end of planar upper member 16 while flange 24 extends downwardly from the outer end of planar lower member 18. The flanges 22 and 24 externally overlie the lips of the patient as illustrated generally in FIG. 2.

Airway 12 also includes a curved section 26 which is comprised of a curved upper member 28 and a curved lower member 30 which are spaced-apart by a continuation of the medial web 20 and which is designated by the reference numeral 20A. As seen, the curved lower member 30 has a generally inverted "V" shape. The width of upper member 28 is substantially the same as the width of the planar upper member 16. The width of the inverted V-shaped curved lower member 30 is greater than the width of planar lower member 18. In the preferred embodiment, the members 28 and 30, at their juncture with the medial web 20A, are spaced-apart at a greater distance than the distance between members 16 and 18. However, due to the inverted "V" shape of member 30, there are some situations where the member 28 and 30, at their juncture with the medial web 20A, are spaced-apart the same distance as the members 16 and 18.

Figure 6:
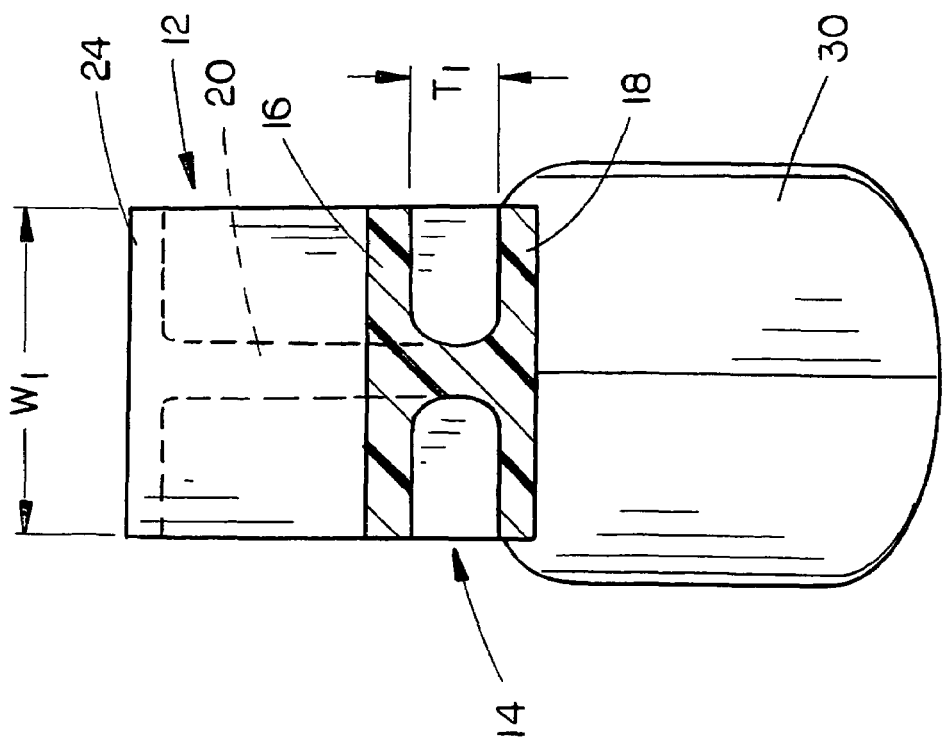
FIG. 6 is a sectional view as seen on lines 6-6 of FIG. 5.

FIG. 6 illustrates a cross-sectional view of the straight section 14 of the oral airway 12 wherein it can be seen that the width $W_1$ of the flange 24 is less than the width of the member 30. FIG. 6 also illustrates as $T_1$ the distance or spacing between members 16 and 18 of straight section 14.

Figure 7:
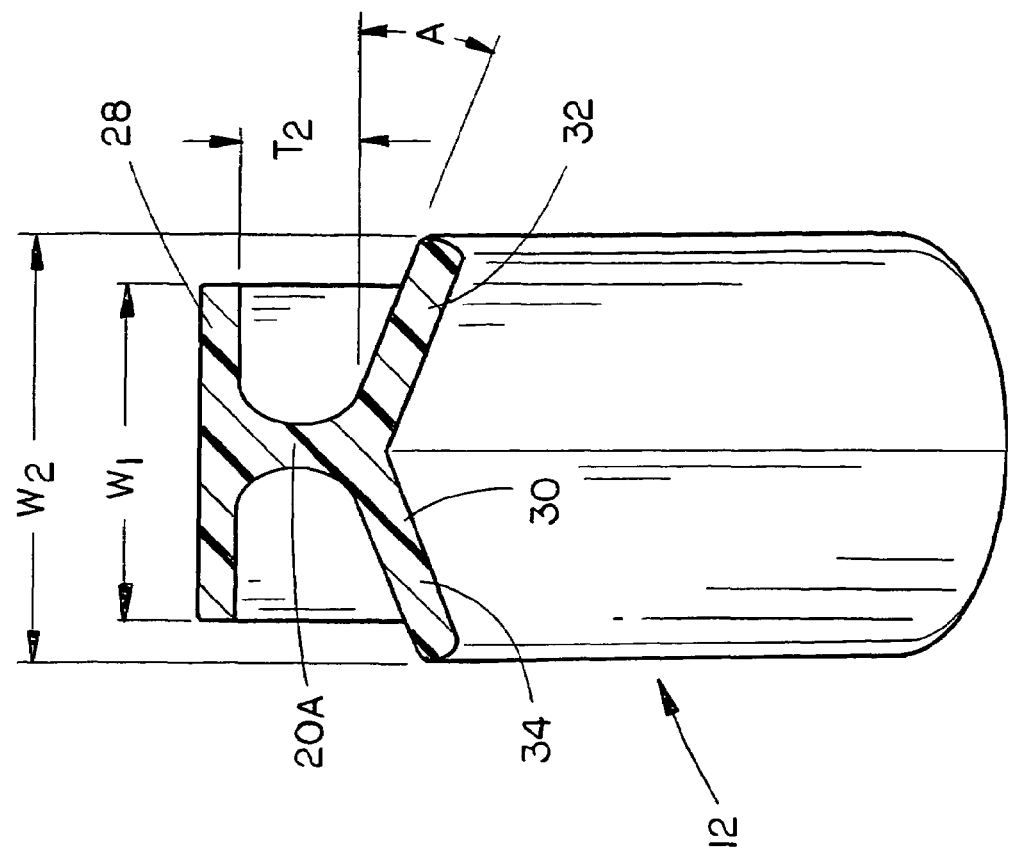
FIG. 7 is a sectional view as seen on lines 7-7 of FIG. 5.

As seen in FIG. 7, the width of member 30 ($W_2$) is greater than the width of member 28 ($W_1$) and that the distance between members 28 and 30 at their juncture with the medial web 20A is greater than the distance $T_1$ between member 16 and 18. FIG. 7 also illustrates that the sides 32 and 34 of member 30 are disposed at an angle A to provide the inverted "V" shape of member 30.

Therefore, the present invention provides modifications to the Berman Oral Airway which will provide better elevation to the tongue against the floor of the mouth by way of: 1) a longer middle support distance which increases the distance the tongue is elevated against the floor of the mouth thus increasing the anterior-posterior dimension of the airway opening; 2) the greater width of the lower member 30 which will give better support to the tongue laterally, thus increasing the side to side dimension of the airway opening; and (3) the elevation of the lower curved member of the curved section of the airway into an inverted "V" shape which will also greatly increase the lateral support of the tongue.

By altering the three dimensions of the Berman Oral Airway, but not altering the length or the radius of the curve of the airway, the size of the oral airway of this invention would be interchangeable with the Berman Oral Airway sizes. For instance, in a situation wherein a person would normally use an 80 mm Berman Oral Airway, the 80 mm airway of this invention would be appropriate, but would give better tongue support and consequently a larger opening of the patient's airway to facilitate easier ventilation of the patient. This would be especially helpful in obese patients with large tongues, but would also be useful for all patients being administered general anesthesia.

Thus it can be seen that the invention accomplishes at least all of its stated objectives.

I claim:

1. An oral airway to provide an air passage to a patient's trachea, comprising:
   a straight section having inner and outer ends adapted to fit between the patient's teeth;
   a curved section adapted to fit over the patient's tongue and extending to the oropharyngeal area;
   said straight section including a substantially planar upper member and a substantially planar lower member which are spaced-apart by a medial web extending therebetween;
   said planar upper and lower members of said straight section having substantially the same widths;
   said outer end of said planar upper member having an upwardly extending flange;
   said outer end of said planar lower member having a downwardly extending flange;
   said flanges adapted to be externally overlying the lips of the patient;
   said curved section comprising spaced-apart curved upper and lower members which are spaced-apart by a medial web extending therebetween;
   said curved lower member having substantially the same width for its entire length;
   said curved upper member of said curved section having substantially the same width as said planar upper member of said straight section;
   said curved lower member of said curved section having a greater width for substantially its entire length than said planar lower member of said straight section and said curved upper member;
   said curved lower member of said curved section having a generally inverted V-shaped cross-section;
   each of said curved lower member and said curved upper member of said curved section having side edges;
   the distance between the side edges of said curved lower member and said curved upper member of said curved section being greater than the distance between the side edges of said planar upper and lower members of said straight section;
   the distance between the side edges of said curved lower member and said curved upper member of said curved section being substantially constant for substantially the entire length of said curved section.

2. An oral airway to provide an air passage to a patient's trachea, comprising:
   a straight section having inner and outer ends adapted to fit between the patient's teeth;
   a curved section adapted to fit over the patient's tongue and extending to the oropharyngeal area;
   said straight section including a substantially planar upper member and a substantially planar lower member which are spaced-apart by a medial web extending therebetween;
   said planar upper and lower members of said straight section having substantially the same widths;
   said outer end of said planar upper member having an upwardly extending flange;
   said outer end of said planar lower member having a downwardly extending flange;
   said flanges adapted to be externally overlying the lips of the patient;
   said curved section comprising spaced-apart curved upper and lower members which are spaced-apart by a medial web extending therebetween;
   said curved lower member having substantially the same width for its entire length;
   said curved upper member of said curved section having substantially the same width as said planar upper member of said straight section;
   said curved lower member of said curved section having a greater width for substantially its entire length than said planar lower member of said straight section and said curved upper member;
   said curved lower member of said curved section having a generally inverted V-shaped cross-section;
   each of said curved lower member and said curved upper member of said curved section having side edges;
   the distance between the side edges of said curved lower member and said curved upper member of said curved section being greater than the distance between the side edges of said planar upper and lower members of said straight section;
   the distance between the side edges of said curved lower member and said curved upper member of said curved section being constant for substantially the entire length of said curved section.

* * * * *